United States Patent
Peschel et al.

(10) Patent No.: US 6,943,274 B2
(45) Date of Patent: Sep. 13, 2005

(54) METHOD FOR THE PRODUCTION OF CYCLOHEXANOL FROM BENZENE

(75) Inventors: Werner Peschel, Freinsheim (DE); Till Adrian, Bobenheim-Roxheim (DE); Harald Rust, Neustadt (DE); Arnd Böttcher, Frankenthal (DE); Thomas Hill, Ludwigshafen (DE); Ulrich Müller, Neustadt (DE); Rainer Papp, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/505,705

(22) PCT Filed: Feb. 28, 2003

(86) PCT No.: PCT/EP03/02049
§ 371 (c)(1),
(2), (4) Date: Aug. 26, 2004

(87) PCT Pub. No.: WO03/074453
PCT Pub. Date: Sep. 12, 2003

(65) Prior Publication Data
US 2005/0148803 A1 Jul. 7, 2005

(30) Foreign Application Priority Data
Mar. 6, 2002 (DE) .................. 102 09 701

(51) Int. Cl.$^7$ ............................ C07C 29/20
(52) U.S. Cl. ...................... 568/835
(58) Field of Search ....................... 568/835

(56) References Cited

U.S. PATENT DOCUMENTS 4,067,915 A * 1/1978 Yasuhara et al. ............ 570/212
4,339,604 A * 7/1982 van Geem et al. .......... 568/357
4,927,974 A * 5/1990 van Geem et al. .......... 568/357

FOREIGN PATENT DOCUMENTS

CA 2388881 5/2001

OTHER PUBLICATIONS

Ullmann's Encyclopedia of Industrial Chemistry, 5$^{th}$ Ed., vol. A 8, VCH Verlagsgesellschaft mbH, Weinheim, Deutschland, 1987, p. 222.
Ullmann's Encyclopedia of Industrial Chemistry, 5th Ed. vol. A8 p 221 (1987).

* cited by examiner

Primary Examiner—Michael L. Shippen
(74) Attorney, Agent, or Firm—Novak Druce & Quigg

(57) ABSTRACT

A process for preparing cyclohexanol from benzene by:
a) preparing cyclohexene by hydrogenating benzene in the presence of a catalyst, and
b) preparing cyclohexanol by hydrating the cyclohexene in the presence of a catalyst, comprises:
carrying out steps a) and b) in a reaction facility which has a bottom region at the lower end,
a top region at the upper end, and
a reaction zone between the top region and the bottom region which contains the catalyst according to steps a) and b),
evaporating a portion of the benzene using the heat of reaction in the reaction zone, condensing it in the top region and returning it to the reaction zone, and
withdrawing a reaction mixture containing cyclohexanol in the bottom region.

7 Claims, No Drawings

METHOD FOR THE PRODUCTION OF CYCLOHEXANOL FROM BENZENE

The present invention relates to a process for preparing cyclohexanol from benzene by:
a) preparing cyclohexene by hydrogenating benzene in the presence of a catalyst, and
b) preparing cyclohexanol by hydrating the cyclohexene in the presence of a catalyst, which comprises:
   carrying out steps a) and b) in a reaction facility which has a bottom reaction at the lower end,
   a top reaction at the upper end, and
   a reaction zone between the top reaction and the bottom reaction which contains the catalyst according to steps a) and b),
   evaporating a portion of the benzene using the heat of reaction in the reaction zone, condensing it in the top reaction and returning it to the reaction zone, and
   withdrawing a reaction mixture containing cyclohexanol in the bottom reaction.

According to Ullmann's Encyclopedia of Industrial Chemistry, 5th Edition, Volume A8, VCH Verlagsgesellschaft mbH, Weinheim, Germany, 1987, page 222, $6^{th}$ paragraph, cyclohexanol is an important intermediate in preparing adipic acid and caprolactam which are both monomers for preparing important polymers, such as nylon 6 and 66. In addition, cyclohexanol finds use as a solvent and cleaning agent and in preparing plasticizers, insecticides and fragrances.

Various continuous processes are known for preparing cyclohexanol.

According to Ullmann's Encyclopedia of Industrial Chemistry, loc cit., p. 221, paragraph 2.4., one of these comprises the hydrogenation of benzene to cyclohexene in the presence of a catalyst and the hydration of the cyclohexene in the presence of a catalyst to cyclohexanol.

As is well known, there are two main problems in this process: the undesirably high extent of cyclohexane formation from the hydrogenation of benzene to cyclohexane and the subsequent difficult removal of cyclohexene from the benzene/cyclohexane/cyclohexene mixture.

In order to suppress overhydrogenation of benzene to cyclohexane, the hydrogenation may be carried out using only partial benzene conversion. However, this has the disadvantage that relatively large apparatus is required for the hydrogenation and that in addition it is necessary to remove unconverted benzene, as well as the cyclohexane which occurs despite the only partial conversion of benzene, from the product mixture. Since benzene and cyclohexane form an azeotrope, but only benzene can be hydrogenated to cyclohexene, the separation of the reaction products in this process variant also presents considerable problems.

It is an object of the present invention to provide a process which allows the preparation of cyclohexanol from benzene in a technically simple and economical manner while avoiding the abovementioned disadvantages.

We have found that this object is achieved by a process as defined at the outset.

According to the invention, the preparation of cyclohexanol from benzene is carried out in a reaction facility which has:
   a bottom reaction at the lower end,
   a top reaction at the upper end, and
   a reaction zone between the top reaction and the bottom reaction which contains the catalyst according to steps a) and b).

Preferred reaction facilitys include distillation columns as described, for example, in Kirk-Othmer, Encyclopedia of Chemical Technology, $3^{rd}$ Ed., Vol. 7, John Wiley & Sons, New York, 1979, pages 870–881, such as tray columns, for example sieve tray columns or bubble cap tray columns, columns with structured or random packings. Particular preference is given to columns with structured packings.

The reaction zone may be disposed within the distillation column.

The reaction zone may be disposed outside the distillation column. In this case, the pressure in the reaction zone and the pressure in the distillation column may be identical or different.

In a preferred embodiment, the reaction facility may contain a further zone ("separating zone") between the bottom reaction and reaction zone which is free of catalysts from step a) and step b) and has a theoretical number of plates in the range from 5 to 50, preferably from 20 to 40, in particular from 15 to 25.

An advantageous further zone is the separating section of a distillation column, which is that section of a distillation column that is disposed between the bottom section and the top section of a customary distillation column, as described in, for example: Kirk-Othmer, Encyclopedia of Chemical Technology, $3^{rd}$ Ed., Vol. 7, John Wiley & Sons, New York, 1979, pages 870–881, such as tray columns, for example sieve tray columns or bubble cap tray columns, columns with structured or random packings.

In a particularly preferred embodiment, the reaction facility is a pressure column.

The process according to the invention can advantageously be carried out at a pressure in the range from 0.1 to 3.5 MPa, preferably from 0.5 to 2.5 MPa.

This results in temperatures in the reaction zone in the range from 70 to 220° C., preferably from 120 to 190° C.

In a further preferred embodiment, the reaction facility may have a means of withdrawing gases at the upper end of the top section.

According to the invention, the reaction zone contains catalysts suitable for carrying out the reactions in steps a) and b). In principle, useful catalysts include those known per se for steps a) and b).

In a preferred embodiment, catalysts can be used in step a) which use at least one element of group VIII, preferably ruthenium, as the catalytically active component or mixtures of these elements can be used as catalyst. If desired, such catalysts may contain at least one further transition metal of a group other than VIII, preferably zinc, or mixtures of such metals, as a dopant.

Such catalysts are described, for example, in EP-A-1048349.

In a further preferred embodiment, a catalyst can be used in step b) which comprises at least one zeolite, such as ZSM-5, ZSM-11, ZBM-10, MCM-22, MCM-36, MCm-49 or PSH-3, or or a mixture thereof.

Such catalysts are described, for example, in DE-A-19951280.

In a particularly preferred embodiment, mixtures of the catalysts mentioned for step a) and step b) may be used.

In a very particularly preferred embodiment, a bifunctional catalyst may be used which simultaneously catalyzes steps a) and b).

The quantities of catalyst for steps a) and b) may be easily determined using the catalyst space velocities known for these catalysts for each reaction and the conversions chosen in the process according to the invention, and the catalyst quantities may be easily optimized by a few simple preliminary experiments.

Benzene is advantageously added to the top region of the reaction facility, in particular in the liquid phase.

Water is also advantageously added to the top region of the reaction facility, in particular in the liquid phase.

In particular, benzene and water may be added as a liquid phase mixture to the top reaction of the reaction facility.

The mixing ratio of benzene to water is determined by the stoichiometry of the reaction and also by the water quantity withdrawn in the bottom reaction. A particularly useful mixing ratio of benzene to water is in the range from 1:2 to 5:1 mol/mol, preferably from 1:1 to 3:1 mol/mol.

The hydrogen required for the reaction may advantageously be added to the reaction facility below the reaction facility. When the reaction zone contains a separating zone, preference is given to adding the hydrogen to the reaction facility between the separating zone and the reaction zone.

The mixing ratio of benzene to hydrogen is determined by the stoichiometry of the reaction and also by the quantity of cyclohexane withdrawn in the bottom reaction.

The reactions taking place in the reaction zone are exothermic overall, i.e. generate heat. According to the invention, the reaction is carried out by using the heat of reaction to evaporate a portion of the benzene, condensing it in the top reaction and returning it to the reaction zone.

According to the invention, a reaction mixture is withdrawn in the bottom reaction which contains cyclohexanol.

In an advantageous embodiment, the reaction mixture contains less than 10% by weight, preferably less than 1% by weight, of benzene, and in particular the reaction mixture is free of benzene.

The selectivity for cyclohexanol in steps a) and b), based on benzene, and the benzene content of the reaction mixture withdrawn in the bottom reaction may advantageously be controlled by means of the energy input into the reaction facility, in particular in the bottom reaction.

Advantageously, the conversion is controlled in such a manner that the reaction mixture, based on the total weight of the reaction mixture, consists of:
from 20 to 40% by weight, in particular from 25 to 30% by weight, of cyclohexanol,
from 40 to 70% by weight, in particular from 50 to 70% by weight, of cyclohexane,
from 1 to 10% by weight, in particular from 2 to 10% by weight, of water,
and any remainder of benzene, although preferably none.

The achievement of the underlying object of the present invention by the process according to the invention is surprising, since, as is well known, the hydrogenation of cyclohexene to cyclohexane is rapid, but the hydration of cyclohexene to cyclohexanol is slow and, in addition, said hydration is an equilibrium reaction which lies on the side of cyclohexene.

EXAMPLE 1

A pressure column of 70 mm diameter having a bottom region, a separating zone having 20 bubble cap trays, a reaction zone which contains 750 cm$^3$ of a catalyst comprising 0.1% by weight of ruthenium and 0.1% by weight of zinc on ZBM-10 extrudates (1.5 mm diameter) in Montz Katapak, and a top region was charged with a liquid mixture of 500 g/h of benzene and 38 g/h of water at 95° C. in the top region and with 34 g/h of hydrogen between the reaction zone and the separating zone at a column pressure of 1.216 MPa (12 bar) measured in the bottom region. The temperature in the bottom region was 180° C., the energy input in the bottom region 0.6 kw.

The reaction mixture withdrawn in the bottom reaction resulting from the benzene, water and hydrogen quantities added had the following composition:
29% by weight of cyclohexanol
61% by weight of cyclohexane
10% by weight of water
no benzene.

We claim:

1. A process for preparing cyclohexanol from benzene by:
    a) preparing cyclohexene by hydrogenating benzene in the presence of a catalyst and
    b) preparing cyclohexanol by hydrating the cyclohexene in the presence of a catalyst, which comprises:
        carrying out steps a) and b) in a reaction facility which has a bottom region at the lower end,
        a top region at the upper end, and
        a reaction zone between the top region and the bottom region which contains the catalyst according to steps a) and b),
        evaporating a portion of the benzene using the heat of reaction in the reaction zone, condensing it in the top region and returning it to the reaction zone, and
        withdrawing a reaction mixture containing cyclohexanol in the bottom region.

2. A process as claimed in claim 1, wherein the benzene is introduced into the top region.

3. A process as claimed in claim 1, wherein the selectivity for cyclohexanol from steps a) and b), based on benzene, is controlled by means of the energy input into the bottom region.

4. A process as claimed in claim 1, wherein the reaction mixture withdrawn from the bottom region is free of benzene and cyclohexene.

5. A process as claimed in claim 1, wherein a further zone is disposed between the bottom region and the reaction zone which is free of the catalysts from steps a) and b) and has a theoretical number of plates in the range from 5 to 50.

6. A process as claimed in claim 1, wherein the process is carried out at a pressure in the range from 0.1 to 3.5 MPa, measured in the bottom region of the reaction facility.

7. A process as claimed in claim 1, wherein the reaction facility used is a distillation column.

* * * * *